United States Patent [19]

Majeti

[11] Patent Number: 5,599,554
[45] Date of Patent: Feb. 4, 1997

[54] TREATMENT OF NICOTINE CRAVING AND/OR SMOKING WITHDRAWAL SYMPTOMS

[75] Inventor: Satyanarayana Majeti, Cincinnati, Ohio

[73] Assignee: The Procter & Gamble Company, Cincinnati, Ohio

[21] Appl. No.: 619,860

[22] Filed: Mar. 19, 1996

Related U.S. Application Data

[63] Continuation of Ser. No. 264,654, Jun. 23, 1994, abandoned.

[51] Int. Cl.$^6$ ..................................................... A61F 13/02
[52] U.S. Cl. .......................... 424/448; 424/434; 424/435; 424/449; 514/813
[58] Field of Search ..................................... 424/448, 449, 424/434, 435; 514/813

[56] References Cited

U.S. PATENT DOCUMENTS

| | | | |
|---|---|---|---|
| 3,598,122 | 8/1971 | Zaffaroni et al. | 128/268 |
| 4,568,676 | 2/1986 | Smith | 514/258 |
| 4,597,961 | 7/1986 | Etscorn | 424/28 |
| 4,671,953 | 6/1987 | Stanley et al. | 424/440 |
| 4,713,243 | 12/1987 | Schiraldi et al. | 424/676 |
| 4,778,677 | 10/1988 | Ebbesen | 424/128 |
| 4,806,356 | 2/1989 | Shaw | 424/440 |
| 4,863,737 | 9/1989 | Stanley et al. | 424/440 |
| 4,883,660 | 11/1989 | Blackman et al. | 424/78 |
| 4,900,552 | 2/1990 | Sanvordeker et al. | 424/422 |
| 4,929,508 | 5/1990 | Sharma et al. | 424/439 |
| 4,959,380 | 9/1990 | Wilson | 514/356 |
| 4,980,169 | 12/1990 | Oppenheimer et al. | 424/439 |
| 5,051,426 | 9/1991 | Parnell | 514/263 |
| 5,288,497 | 2/1994 | Stanley et al. | 424/440 |
| 5,288,498 | 2/1994 | Stanley et al. | 424/440 |
| 5,298,501 | 9/1993 | Parnell | 424/195.1 |

FOREIGN PATENT DOCUMENTS

| | | | |
|---|---|---|---|
| 0192950 | 9/1986 | European Pat. Off. | A61M 15/06 |
| 0563507 | 10/1993 | European Pat. Off. | A61K 9/70 |
| 91/03998 | 4/1991 | WIPO | A61F 13/02 |

OTHER PUBLICATIONS

Cohen, C., et al., "Caffeine Antagonizes EEG Effects of Tobacco Withdrawal", Pharmacology Biochemistry and Behavior, vol. 47, No. 4, pp. 919–926 (Apr., 1994).

Tariq, M., et al., "Effect of Nicotine and Caffeine Pretreatment on the Gastric Mucosal Damage Induced by Aspirin, Phenylbutazone, and Reserpine in Rats", Toxicology and Applied Pharmacology, vol. 79, No. 2, pp. 268–273 (Jun. 30, 1985).

Wilson, Steven P., "Pertussis Toxin Enhances Proenkephalin Synthesis in Bovine Chromaffin Cells", Journal of Neurochemistry, vol. 61, No. 5, pp. 1901–1906 (Nov., 1993).

*Primary Examiner*—D. Gabrielle Phelan
*Attorney, Agent, or Firm*—Mary Catherine Poland; Douglas C. Mohl; Jacobus C. Rasser

[57] ABSTRACT

The subject invention encompasses a transdermally or transmucosally administrable composition for the treatment or nicotine craving or smoking withdrawal symptoms comprising nicotine and caffeine or caffeine equivalent.

10 Claims, No Drawings

TREATMENT OF NICOTINE CRAVING AND/OR SMOKING WITHDRAWAL SYMPTOMS

This is a continuation of application Ser. No. 08/264,654, filed on Jun. 23, 1994, now abandoned.

BACKGROUND OF THE INVENTION

The health hazards from smoking tobacco are well known. Of the many by-products of combustion found in cigarette smoke, the substances most studied have been tars, carbon monoxide, and nicotine. Tars are the agents linked to the causation of various cancers and pulmonary diseases such as emphysema and chronic bronchitis. Carbon monoxide is a deadly gas which reduces the ability of blood hemoglobin to carry sufficient oxygen. Carbon monoxide has also been causally linked to coronary artery disease and atherosclerosis. Nicotine appears to be the most pharmacologically active substance in tobacco smoke, yet it seems not to be as significant from a health standpoint as the tars and carbon monoxide. However, nicotine is the reinforcing substance in tobacco which maintains the addiction.

Various efforts have been made by smokers to discontinue smoking. Chewing beeswax, eating candy and peppermints, as well as cold turkey interruption have been tried without much success. The addition of chemicals designed to sicken the user or otherwise render smoking repulsive to the user have also not produced good results. More recent therapies for smoking cessation have focused on the administration of nicotine to the smoker. These therapies allow the individual to satisfy a nicotine habit while minimizing or eliminating side effects caused by absorbing nicotine through the lungs along with the other harmful by-products of combustion of tobacco.

Nicotine supplementation has proven to be an effective therapy as an adjunct to smoking cessation in helping to reduce the craving for smoking and provide relief from smoking withdrawal symptoms. However, there are many smokers for whom nicotine supplementation alone is inadequate. In accordance with the present invention, it has been discovered that a composition can be formulated which provides the combination of nicotine and caffeine or caffeine equivalent in a single therapy. It has also been discovered that such a combination may offer the advantage of providing treatment and/or relief of nicotine craving and/or smoking withdrawal symptoms to a broader spectrum of smokers who wish to break the smoking habit. It has further been discovered that these compositions may also curb the appetite which may aid in reducing the weight gain that is commonly experienced by individuals who stop smoking.

It is an object of the present invention to provide a composition comprising the combination of nicotine and caffeine or caffeine equivalent in a single therapy. It is also an object of the present invention to deliver the nicotine and caffeine combination therapy in a convenient delivery system. It is a further object of the invention to provide a method for the treatment and/or relief of nicotine craving and/or smoking withdrawal symptoms in individuals who wish to break or decrease the habit of smoking tobacco or the use of any tobacco product. These and other objects will become readily apparent from the detailed description which follows.

SUMMARY OF THE INVENTION

The present invention relates to a transdermally or transmucosally administrable composition for the treatment of nicotine craving and/or smoking withdrawal symptoms comprising nicotine and caffeine or caffeine equivalent, wherein the composition delivers from about 1 mg to about 100 mg of nicotine, and from about 10 mg to about 250 mg of caffeine or caffeine equivalent.

The present invention also relates to a method for providing treatment and/or relief of nicotine craving and/or smoking withdrawal symptoms to a human or lower animal in need of such treatment comprising the administration of a safe and effective amount of a transdermally or transmucosally administrable composition comprising nicotine and caffeine or caffeine equivalent.

DETAILED DESCRIPTION OF THE INVENTION

The subject invention comprises nicotine, caffeine or caffeine equivalent, and preferably one or more pharmaceutically-acceptable carriers suitable for transdermal and/or transmucosal administration. These compositions are useful for the treatment and/or relief of nicotine craving and/or smoking withdrawal symptoms.

The terms "nicotine craving" and "smoking withdrawal symptoms" as used herein both refer to any physical or psychological reaction relating to breaking the habit of smoking tobacco or using any tobacco product or decreasing the frequency or intensity of smoking tobacco or using any tobacco product.

In general, the descriptive term "pharmaceutically-acceptable" is used herein to describe materials that are non-toxic and suitable for administration to humans and/or lower animals. The term "pharmaceutically-acceptable carder" as used herein means any material safe and effective for use in the compositions of the present invention. Such materials include pH adjusters, emollients, emulsifiers, buffering agents, solvents, preservatives, pressure-sensitive adhesive foming polymers, film forming polymers, bioadhesive and mucoadhesive polymers, water, wetting agents, thickeners, plasticizers, disintegration agents, humectants, surfactants, aromatic compounds, agents for aiding the film-forming properties and substantivity of the formulations, antimicrobials for maintaining the antimicrobial integrity of the compositions, antioxidants, agents suitable for aesthetic purposes such as fragrances, pigments, and colorings, non-soluble ingredients, any material suitable or transdermal or transmucosal carriers, and mixtures thereof.

The terms "safe and effective amount", as used herein, mean a sufficient amount of material to provide the desired benefit without undue adverse side effects commensurate with a reasonable benefit/risk ratio when used in the manner of this invention. The specific safe and effective amount will vary with such factors as the particular condition that is being treated, the severity of the condition, the duration of the treatment, the physical condition of the patient, the nature of concurrent therapy (if any), and the specific formulation and optional components hereinafter.

The terms "suitable for transdermal and/or transmucosal administration" and "transdermally or transmucosally administrable", as used herein, refer to any composition or formulation that is suitable for the convenient administration of the composition whereby the nicotine and caffeine or caffeine source is absorbed through the skin or oral mucosa.

The following terms will be designated as follows: milligram as "mg", milliliter as "ml", nanogram as "ng", and microgram as "ug".

A detailed description of essential and optional components of the present invention is given below.

Nicotine

The present invention comprises nicotine. Nicotine is a tertiary amine composed of a pyridine and a pyrrolidine ring. It is a colorless to pale yellow, which is freely water soluble, strongly alkaline, hygroscopic liquid obtained from the tobacco plant. Nicotine has a characteristic odor and turns brown on exposure to air or light [*Physicians Desk Reference*, 48th Edition, p. 1306, 1984] Nicotine is delivered in an amount of from about 1 mg to about 100 mg, preferably from about 5 mg to about 75 mg, and most preferably from about 10 mg to about 50 mg. Nicotine is also described in *Remington's Pharmaceutical Sciences*, 18th Edition, 1990, p. 891, which is incorporated herein by reference.

Caffeine

The present inventions also comprise caffeine or a caffeine equivalent. Caffeine is found as white, fleecy masses or long, flexible, silky crystals. It is odorless, bitter tasting, and slightly soluble in water and alcohol. Caffeine may be derived synthetically or by extraction of coffee beans, tea leaves or kola nuts [*Hawley's Condensed Chemical Dictionary*, Twelfth Edition, 1993]. Examples of suitable sources of caffeine for use in the present invention are pure caffeine, caffeine combined with acetate, citrate, benzoate, phosphate, sulfate or salicylate. Also suitable are any of the xanthine analogues that match caffeine's effectiveness as a central nervous system stimulant, including salts thereof that are compatible. Xanthine derivatives are described in *Reminton's Pharmaceutical Sciences*, 18th Edition, 1990, pp. 1132–34, which is incorporated herein by reference. The caffeine or caffeine equivalent is delivered in an amount of from about 10 mg to about 250 mg, preferably from about 50 mg to about 200 mg, and most preferably from about 75 mg to about 100 mg.

Pharmaceutically-Acceptable Aqueous Carrier

The invention compositions preferably also contain one or more pharmaceutically-acceptable carriers suitable for transdermal and/or transmucosal administration. Such compositions include (but are not limited to) transdermal and buccal patches, bioadhesive and mucoadhesive films or other formulations suitable administering the present compositions transdermally and/or transmucosally.

The present compositions also include formulations which deliver the nicotine and/or caffeine or caffeine equivalent in a sustained release system or at varying intervals or levels throughout the transdermal or transmucosal administration of the composition. Transdermal drug delivery systems are fully described in *Pharmaceutical Dosage Forms and Drug Delivery Systems*, Howard C. Ansel, Ph.D. and Nicholas G. Popovich, Ph.D., Fifth Edition, 1990, pp. 310–320, U.S. Pat. No. 3,598,122, to Zaffaroni, issued Aug. 10, 1971, and U.S. Pat. No. 4,713,243, to Schiraldi, et. al., issued Dec. 15, 1987, all of which is incorporated herein by reference.

While the choice of transdermal or transmucosal carrier is not critical to the present invention, the carrier or carriers chosen must be suitable for administering the nicotine and caffeine or caffeine equivalent so that the desired blood levels of these compounds are achieved in the body of the recipient. The desired blood level of nicotine is from about 1 ng/ml to about 100 ng/ml, preferably from about 5 ng/ml to about 75 ng/ml, and most preferably from about 10 ng/ml to about 50 ng/ml, preferably within 1 to 4 hours of administration. The desired blood level of caffeine or caffeine equivalent is from about 0.01 ug/ml to about 20 ug/ml, preferably from about 0.1 ug/ml to about 15 ug/ml, and most preferably from about 0.5 ug/ml to about 10 ug/ml, preferably within 1–4 hours of administration.

The present compositions will normally be prepared in dosage unit form to contain safe and effective amounts of the nicotine and caffeine (or equivalent) to achieve the desired blood levels. Fractions of the dosage units or multiple dosage units may also be utilized. In general, the transdermally or transmucosally administrable compositions deliver to a human or lower animal from about 1 mg to about 100 mg, preferably from about 5 mg to about 75 mg, and most preferably from about 10 mg to about 50 mg of nicotine; and from about 10 mg to about 250 mg, preferably from about 50 mg to about 200 mg, and most preferably from about 75 mg to about 100 mg, of caffeine or caffeine equivalent. Preferably, the present invention may be a transdermally or transmucosally administrable composition for the treatment of nicotine craving and/or smoking withdrawal symptoms comprising nicotine, caffeine or caffeine equivalent, and one or more pharmaceutically-acceptable carders suitable for transdermal or transmucosal administration, wherein the composition delivers from about 1 mg to about 100 mg of nicotine, and from about 10 mg to about 250 mg of caffeine or caffeine equivalent.

The amount of nicotine and caffeine or caffeine equivalent and frequency of administration may vary depending on the carrier chosen and the personal needs of the user. However, it is suggested (as an example) that the present invention be administered from about once per day to once per week, preferably from about once per day to about 3 times per week, and most preferably about once per day.

The transdermal or transmucosal carriers of the present invention may comprise a single layer or multi-layer system. Typically these carriers comprise an adhesive layer, which in a single layer system, releases the nicotine and caffeine or caffeine equivalent. The adhesive layer may be mucoadhesive, bioadhesive, pressure sensitive or require moisture for adhesion. Multi-layer systems generally will also comprise at least one reservoir layer, a backing component, and may include other layers of varying solubility which aid in controlling the release rate of actives being administered.

Any of the dermatologically acceptable pressure-sensitive adhesives which permit drug migration can be used in the present compositions. Exemplary adhesives include acrylic resins such as polymers of esters of acrylic acid with alcohols (not limited to) n-butanol, n-pentanol, isopentanol, 2-methyl butanol, 2-methyl pentanol, or n-decanol, alone or copolymerized with ethylenically unsaturated monomers such as acrylic acid, methacrylic acid, glycol diacrylates, or mixtures thereof; elastomeric silicone polymers; polyurethane elastomers; rubbery polymers; vinyl polymers such as polyvinylalcohol, polyvinyl pyrrolidone, and polyvinylacetate; cellulose derivatives such as ethyl cellulose, methyl cellulose and carboxymethyl cellulose; natural gums such as guar, acacia, pectins, and the like; and mixtures thereof. Preferred for use in with the oral mucosa are rubbery polymers such as polyisobutylene, with or without gum modifiers, polyvinyl alcohol, polyvinyl pyrrolidone, cellulose derivatives, and mixtures thereof.

Water soluble or water swellable polymers may comprise the adhesive layer to create a bioadhesive or mucoadhesive film. Suitable polymers include hydroxypropyl cellulose, polyethylene oxide homopolymers, alkyl or polyvinyl ether-maleic maleic acid copolymers, polyacrylic acid, polyvinylpyrrolidone, and mixtures thereof. An exemplary adhesive layer which adheres to wet mucosal surfaces comprises from about 40% to about 95% of hydroxypropyl cellulose, from about 5% to about 60% of a homopolymer of ethylene oxide, and from about 2% to about 10% of a glycol plasticizer. The adhesive layer will generally have a thickness of from about 0.01 millimeters to about 7 millimeters, though such limits are not critical to the practice of the present invention.

The compositions of the present invention may also contain a reservoir layer. The reservoir layer may be formed by materials capable of forming film walls or matrixes which allow the nicotine and caffeine or caffeine equivalent to pass by diffusion. Materials for use in a reservoir layer include without limitation: silicone rubbers such as conventional heat-curable silicones or room temperature vulcanizable silicone rubbers, poly(hydroxyethylacrylate) and poly(hydroxyethylmethacrylate), polyvinylalcohol, polyvinylacetate, plasticized polyvinylchloride, polyvinylpyrrolidone plus mannitol, plasticized nylon, collagen, gelatin, waxes such as polyethylene wax, oxidized polyethylene wax, hydrogenated castor oil, and the like.

The present inventions may also contain a backing component to prevent the passage of the drug through surface of the delivery vehicle opposite the skin or oral mucosa. The backing member component can be flexible or nonflexible. Materials useful as the backing component include cellophane, cellulose acetate, cellulose acetate isobutyrate, cellulose acetate propionate, ethylcellulose, plasticized vinylacetate-vinylchloride copolymers, polyethylene terephthalate, nylon, polyethylene, polyurethanes, rubber based polyisobutylene, styrene, and styrene-butadiene copolymers, polyvinylidene chloride, and the like. If the outer surface of the reservoir layer is durable enough and impermeable to the nicotine and caffeine or caffeine equivalent, the backing component may be unnecessary.

Various polymers may be incorporated into one or more of the transdermal or transmucosal carriers to modify one or more of the layer's permeability thereby effecting the amount or rate of delivery of the nicotine and/or caffeine (or caffeine equivalent). Useful polymers for modifying permeability include ethyl cellulose, propyl cellulose, polyethylene, polypropylene, carboxymethylcellulose (free acid), and mixtures thereof.

The present compositions may contain one or more solvents. Suitable solvents include but are not limited to water, alcohol, propylene glycol, glycerin, sorbitol solution and the like, to assist solubilization and incorporation of water-insoluble ingredients.

The present compositions may also contain a plasticizer. Suitable plasticizers include glycols such as propylene glycol and polyethylene glycol; polyhydric alcohols such as glycerin and sorbitol, glycerol esters such as glycerol triacetate; fatty acid triglycerides such as NEOBEE M-5 and MYVEROLS; distilled acetylated monoglycerides; sucrose acetate isobutyrate; triacetin; mineral oil; vegetable oils; and mixtures thereof. Preferred plasticizers are triacetin, propylene glycol or polyethylene glycol.

A pharmaceutically-acceptable preservative may be employed to increase the shelf life of the compositions. Benzyl alcohol is suitable, although a variety of preservatives including, for example, parabens, thimerosal, chlorobutanol, phenylmercuric acetate or benzalkonium chloride may also be employed. The most preferred preservatives for use herein include benzalkonium chloride, chlorhexidine gluconate, butylated hydroxy toluene, and disodium EDTA. A suitable concentration of the preservative will be from about 0.001% to about 2% based on the total weight, although there may be appreciable variation depending upon the agent selected.

The compositions of the present invention also include microencapsulation of either the nicotine or caffeine (or caffeine equivalent) or both. Techniques and materials for microencapsulation are well known in the art. Microencapsulation is discussed more fully in Kirk and Othmer's *Encyclopedia of Chemical Technology*, Vol. 13, 2nd Edition, pp. 436–456, which is incorporated herein by reference.

The compositions of the present invention may also contain one or more aromatic components. These aromatics include, for example, menthol, eucalyptol, benzaldehyde (cherry, almond); citral (lemon, lime); neral; decanal (orange, lemon); aldehyde C-8, aldehyde C-9 and aldehyde C-12 (citrus fruits); tolyl aldehyde (cherry, almond); 2,6-dimethyl-octanal (green fruit); 2-dodecenal (citrus, mandarin); thymol; cedar leaf oil, myristica oil, lavender oil, nutmeg oil, turpentine; 3-1-menthoxy propane- 1,2-diol; N-substituted-p-menthane-3-carbox-amides and acyclic carboxamides; and mixtures thereof. Preferred are menthol, eucalyptol, thymol, cedar leaf oil, myristica oil, lavender oil, nutmeg oil, turpentine, and mixtures thereof. Aromatic compounds may be present at a level of from about 0.0001% to about 1%, preferably from about 0.001% to about 1%, and most preferably from about 0.001% to about 0.5%, by weight of the compositions.

A variety of additional optional pharmaceutically-acceptable ingredients may also be added to the present invention compositions. These additional ingredients include pH adjusters such as sodium hydroxide; fillers; disintegration agents such as magnesium silicate, calcium carbonate, stearic acid and its salts, palmitic acid; emulsifiers; binders; dispersants; thickeners; buffering agents such as sodium bicarbonate; various polymers for aiding the film-forming properties and substantivity of the formulations; antimicrobials for maintaining the antimicrobial integrity of the compositions; antioxidants; and agents suitable for aesthetic purposes such as fragrances, pigments, and colorings.

Method of Treatment

The present invention also encompasses a method of treatment. The method of providing treatment and/or relief of nicotine craving and/or smoking withdrawal symptoms to a human or lower animal in need of such treatment, as disclosed herein, comprises the administration of a safe and effective amount of a transdermally or transmucosally administrable composition comprising nicotine and caffeine or caffeine equivalent. Such compositions preferably further comprise one or more pharmaceutically acceptable carriers suitable for transdermal or transmucosal administration.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE I

A single layer transdermal delivery system according to the present invention may be prepared as follows:

| Ingredient | Weight % |
| --- | --- |
| Ethylene Oxide Homopolymer (Polyox WSR-301) | 57.9 |
| Hydroxypropyl Cellulose (Klucel MF) | 26.0 |
| Polyethylene (AC-6A) | 5.0 |
| Propylene Glycol | 3.0 |
| Polyethylene Glycol 400 | 2.0 |
| Butylated Hydroxy Toluene | 0.1 |
| Caffeine | 4.0 |
| Nicotine | 2.0 |

The above ingredients are prepared according to methods known in the art.

EXAMPLE II

A multi-layer buccal dosage form according to the present invention may be prepared as follows:

| Ingredient | Weight % in Each Layer | | |
|---|---|---|---|
| | Drug Reservoir | Adhesive | Barrier |
| Titanium Dioxide | | 5.0 | |
| Sucrose Acetate Isobutyrate | | 3.5 | |
| Alginic Acid | 14.0 | | |
| Flavoring | 10.0 | | |
| Cellulose Acetate Butyrate | 6.5 | 17.5 | 5.0 |
| Polycarbophil[1] | | | 7.0 |
| Polyvinyl Pyrrolidone | 4.0 | | |
| Polyethylene Glycol 800 | | | 2.5 |
| Guar Gum | | | 7.0 |
| Caffeine | 5.0 | | |
| Nicotine | 1.0 | | |
| Triacetin | 4.0 | | 5.0 |
| Solvent | 55.5 | 74.0 | 73.5 |

[1]Carbopol ® from B. F. Goodrich Corp.

The above ingredients are prepared according to methods known in the art.

What is claimed is:

1. A transdermally or transmucosally administrable composition for the treatment of nicotine craving or smoking withdrawal symptoms comprising nicotine, caffeine or xanthine compounds, and one or more pharmaceutically-acceptable carriers suitable for transdermal or transmucosal administration selected from the group consisting of a transdermal patch, buccal patch, bioadhesive film, or mucoadhesive film, or combinations thereof, wherein the composition delivers:

a) from about 5 mg to about 100 mg of nicotine wherein the blood level of nicotine is from about 1 nanogram per milliliter to about 100 nanograms per milliliter; and b) from about 10 mg to about 250 mg of caffeine or xanthine compounds wherein the blood level of caffeine or xanthine compounds is from about 0.01 microgram per milliliter to about 20 micrograms per milliliter.

2. The composition according to claim 1 wherein the composition is in the form of a multi-layer transdermal or transmucosal carrier comprising an adhesive layer and a reservoir layer.

3. The composition according to claim 2 wherein (b) is caffeine.

4. The composition according to claim 1 comprising:

a) from about 5 mg to about 75 mg of nicotine; and b) from about 50 mg to about 200 mg of caffeine or xanthine compounds.

5. The composition according to claim 4 further comprising a pressure-sensitive adhesive layer.

6. The composition according to claim 5 wherein the composition is in the form of a multi-layer transdermal carrier comprising a reservoir layer, and a backing component.

7. The composition according to claim 6 wherein the composition is in the form of a multi-layer transmucosal carrier.

8. The composition according to claim 7 further comprising from about 0.01% to about 5% of one or more flavorings.

9. A method for providing treatment of nicotine craving and smoking withdrawal symptoms to a human or lower animal in need of such treatment comprising the administration of a safe and effective amount of the transdermally or transmucosally administrable composition according to claim 1.

10. A method for providing relief of nicotine craving and smoking withdrawal symptoms in a human or lower animal in need of such treatment comprising the administration of a safe and effective amount of the transdermally or transmucosally administrable composition according to claim 4.

* * * * *